US009105435B1

(12) United States Patent
Musselman

(10) Patent No.: US 9,105,435 B1
(45) Date of Patent: Aug. 11, 2015

(54) ROBUST, RAPID, SECURE SAMPLE MANIPULATION BEFORE DURING AND AFTER IONIZATION FOR A SPECTROSCOPY SYSTEM

(71) Applicant: IONSENSE. INC, Saugus, MA (US)

(72) Inventor: Brian D Musselman, Melrose, MA (US)

(73) Assignee: IONSENSE INC., Saugus, MA (US)

( * ) Notice: Subject to any disclaimer, the term of this patent is extended or adjusted under 35 U.S.C. 154(b) by 0 days.

(21) Appl. No.: 14/530,621

(22) Filed: Oct. 31, 2014

Related U.S. Application Data

(63) Continuation of application No. 13/449,615, filed on Apr. 18, 2012, now Pat. No. 8,901,488.

(60) Provisional application No. 61/476,380, filed on Apr. 18, 2011.

(51) Int. Cl.

| | |
|---|---|
| ***H01J 49/00*** | (2006.01) |
| ***H01J 27/02*** | (2006.01) |
| ***H01J 49/10*** | (2006.01) |
| ***H01J 27/26*** | (2006.01) |
| ***H01J 27/24*** | (2006.01) |

(52) U.S. Cl.
CPC ............... *H01J 27/022* (2013.01); *H01J 27/24* (2013.01); *H01J 27/26* (2013.01); *H01J 49/10* (2013.01)

(58) Field of Classification Search
CPC .................. B01L 2400/043; B01L 2200/0647; G01N 35/0098; H01J 49/04
USPC .......................................................... 250/288
See application file for complete search history.

(56) References Cited

U.S. PATENT DOCUMENTS

| | | | |
|---|---|---|---|
| 3,633,027 | A | 1/1972 | Rhyage |
| 3,957,470 | A | 5/1976 | Dawes |
| 4,016,421 | A | 4/1977 | Hull |
| 4,144,451 | A | 3/1979 | Kambara |
| 4,213,326 | A | 7/1980 | Brodasky |
| 4,542,293 | A | 9/1985 | Fenn |

(Continued)

FOREIGN PATENT DOCUMENTS

| | | |
|---|---|---|
| DE | 102007015542 | 10/2007 |
| EP | 1741120 | 3/2014 |

(Continued)

OTHER PUBLICATIONS

Barber, M. et al., "Fast atom bombardment of solids (F.A.B.): a new ion source for mass spectrometry" J.Chem. Soc. Chem. Commun., 1981, 325.

(Continued)

*Primary Examiner* — Michael Maskell
(74) *Attorney, Agent, or Firm* — Sci-Law Strategies, PC

(57) ABSTRACT

This invention provides for the efficient positioning of a sample to be analyzed by using either magnetic or electro-mechanical fields to retain the sample in the ionization region. In an embodiment of the present invention, the sample is contacted with a sampler device, which is inserted into a chamber and accurately positioned using electro-mechanical devices. In an embodiment of the invention, the influence of an electro-mechanical field on the sampler device enables the sample to be positioned in the ionization region to be contacted by particles that result in ionization of the sample whereby rendering the resulting ions available for analysis.

20 Claims, 10 Drawing Sheets

116
101
121

(56) References Cited

U.S. PATENT DOCUMENTS 4,546,253 A 10/1985 Tsuchiya
4,654,052 A 3/1987 Sharp
4,662,914 A 5/1987 Hansen
4,861,988 A 8/1989 Henion
5,012,052 A 4/1991 Hayes
5,055,677 A 10/1991 Amirav
5,137,553 A 8/1992 Dawes
5,192,865 A 3/1993 Zhu
5,306,412 A 4/1994 Whitehouse
5,352,892 A 10/1994 Mordehai
5,367,163 A 11/1994 Otsuka
5,381,008 A 1/1995 Tanner
5,412,208 A 5/1995 Covey
5,448,062 A 9/1995 Cooks
5,552,599 A 9/1996 Giessmann
5,559,326 A 9/1996 Goodley
5,614,711 A 3/1997 Li
5,624,537 A 4/1997 Turner
5,684,300 A 11/1997 Taylor
5,716,825 A * 2/1998 Hancock et al. ........... 435/286.5
5,736,741 A 4/1998 Bertsch
5,788,166 A 8/1998 Valaskovic
5,868,322 A 2/1999 Loucks, Jr.
5,889,404 A 3/1999 Abdel
5,959,297 A 9/1999 Weinberg
5,997,746 A 12/1999 Valaskovic
6,107,628 A 8/2000 Smith
6,124,675 A 9/2000 Betrand
6,190,559 B1 2/2001 Valaskovic
6,225,623 B1 5/2001 Turner
6,297,499 B1 10/2001 Fenn
6,359,275 B1 3/2002 Bertsch
6,395,183 B1 5/2002 Valaskovic
6,562,211 B1 5/2003 Kunnecke
6,583,408 B2 6/2003 Smith
6,600,155 B1 7/2003 Andrien, Jr.
6,646,256 B2 11/2003 Gourley
6,649,907 B2 11/2003 Ebeling
6,670,608 B1 12/2003 Taylor
6,690,006 B2 2/2004 Valaskovic
6,713,757 B2 3/2004 Tanner
6,717,139 B2 4/2004 Taniguchi
6,723,985 B2 4/2004 Schultz
6,744,041 B2 6/2004 Sheehan
6,744,046 B2 6/2004 Valaskovic
6,784,424 B1 8/2004 Willoughby
6,794,642 B2 9/2004 Bateman
6,803,565 B2 10/2004 Smith
6,806,468 B2 10/2004 Laiko
6,818,889 B1 11/2004 Sheehan
6,861,647 B2 3/2005 Reilly
6,875,980 B2 4/2005 Bateman
6,878,930 B1 4/2005 Willoughby
6,888,132 B1 5/2005 Sheehan
6,914,243 B2 7/2005 Sheehan
6,943,347 B1 9/2005 Willoughby
6,949,739 B2 9/2005 Franzen
6,949,740 B1 9/2005 Sheehan
6,949,741 B2 9/2005 Cody
6,956,205 B2 10/2005 Park
6,977,372 B2 12/2005 Valaskovic
6,979,816 B2 12/2005 Tang
6,987,264 B1 1/2006 Whitehouse
6,992,299 B2 1/2006 Lee
7,015,466 B2 3/2006 Takats
7,019,289 B2 3/2006 Wang
7,034,292 B1 4/2006 Whitehouse
7,041,972 B2 5/2006 Bajic
7,049,584 B1 5/2006 Whitehouse
7,053,368 B2 5/2006 Thakur
7,064,317 B2 * 6/2006 McLuckey et al. ........... 250/282
7,071,464 B2 7/2006 Reinhold
7,081,618 B2 7/2006 Laprade
7,081,621 B1 7/2006 Willoughby
7,095,019 B1 8/2006 Sheehan
7,098,452 B2 8/2006 Schneider
7,112,785 B2 9/2006 Laramee
7,138,626 B1 11/2006 Karpetsky
7,157,698 B2 1/2007 Makarov
7,161,145 B2 1/2007 Oser
7,196,525 B2 3/2007 Sparkman
7,247,495 B2 7/2007 Amirav
7,253,406 B1 8/2007 Sheehan
7,332,345 B2 2/2008 Darrach
7,423,261 B2 9/2008 Truche
7,429,731 B1 9/2008 Karpetsky
7,462,826 B2 12/2008 Schneider
7,544,933 B2 6/2009 Cooks
7,569,812 B1 8/2009 Karpetsky
7,582,864 B2 9/2009 Verentchikov
7,700,913 B2 4/2010 Musselman
7,705,297 B2 4/2010 Musselman
7,714,281 B2 5/2010 Musselman
7,777,181 B2 8/2010 Musselman
7,858,926 B1 12/2010 Whitehouse
7,893,408 B2 2/2011 Hieftje
7,923,681 B2 4/2011 Collings
7,928,364 B2 4/2011 Musselman
7,929,138 B1 4/2011 Webb
7,982,183 B2 7/2011 Makarov
7,982,185 B2 7/2011 Whitehouse
8,003,935 B2 8/2011 Robinson
8,026,477 B2 9/2011 Musselman
8,044,346 B2 10/2011 Kostiainen
RE43,078 E 1/2012 Cody
8,101,910 B2 1/2012 Loboda
8,207,497 B2 6/2012 Musselman
8,217,341 B2 7/2012 Musselman
8,242,459 B2 8/2012 Sun
8,278,619 B2 10/2012 Makarov
8,304,718 B2 11/2012 Ouyang
8,308,339 B2 11/2012 Karpetsky
8,334,507 B1 12/2012 Whitehouse
8,362,418 B2 1/2013 Xu
8,410,431 B2 4/2013 Ouyang
8,421,005 B2 4/2013 Musselman
8,481,922 B2 7/2013 Musselman
8,519,354 B2 8/2013 Charipar
8,525,109 B2 9/2013 Musselman
8,563,945 B2 10/2013 Musselman
RE44,603 E 11/2013 Cody
8,592,756 B2 11/2013 Ouyang
8,592,758 B1 11/2013 Nilles
8,604,423 B2 12/2013 Enke
8,648,295 B2 2/2014 Enke
8,664,000 B2 3/2014 Yang
8,686,351 B2 4/2014 Ouyang
8,704,167 B2 4/2014 Cooks
8,710,437 B2 4/2014 Cooks
8,729,496 B2 5/2014 Musselman
8,754,365 B2 6/2014 Krechmer
8,766,178 B2 7/2014 Ouyang
8,803,085 B2 8/2014 Ouyang
8,816,275 B2 8/2014 Ouyang
8,822,949 B2 9/2014 Musselman
8,853,627 B2 10/2014 Ouyang
8,859,956 B2 10/2014 Ouyang
8,859,957 B2 10/2014 Ouyang
8,859,958 B2 10/2014 Ouyang
8,859,959 B2 10/2014 Ouyang
8,890,063 B2 11/2014 Ouyang
2002/0005478 A1 1/2002 Hillenkamp
2002/0121596 A1 9/2002 Laiko
2002/0121598 A1 9/2002 Park
2002/0162967 A1 11/2002 Atkinson
2002/0185593 A1 12/2002 Doring
2002/0185595 A1 12/2002 Smith
2002/0185606 A1 12/2002 Smith
2003/0052268 A1 3/2003 Doroshenko
2004/0094706 A1 5/2004 Covey
2004/0129876 A1 7/2004 Franzen
2004/0159784 A1 8/2004 Doroshenko
2004/0169137 A1 9/2004 Westphall
2005/0079631 A1 4/2005 Laiko

(56) References Cited

U.S. PATENT DOCUMENTS

2005/0230635 A1 10/2005 Takats
2005/0236374 A1 10/2005 Blankenship
2005/0236565 A1 10/2005 Oser
2006/0071665 A1 4/2006 Blake
2006/0079002 A1 4/2006 Gologan
2006/0097157 A1 5/2006 Ouyang
2006/0163468 A1 7/2006 Wells
2006/0249671 A1 11/2006 Karpetsky
2006/0266941 A1 11/2006 Vestal
2007/0114389 A1 5/2007 Karpetsky
2007/0187589 A1 8/2007 Cooks
2007/0228271 A1 10/2007 Truche
2007/0278397 A1 12/2007 Bateman
2008/0073548 A1 3/2008 Denton
2008/0156985 A1 7/2008 Venter
2008/0202915 A1 8/2008 Hieftje
2008/0217254 A1* 9/2008 Anderson .................... 210/695
2009/0168162 A1* 7/2009 Ham et al. .................... 359/395
2009/0272893 A1 11/2009 Hieftje
2010/0078550 A1 4/2010 Wiseman
2010/0102222 A1 4/2010 Musselman
2010/0140468 A1 6/2010 Musselman
2010/0294925 A1 11/2010 Musselman
2010/0301209 A1 12/2010 Ouyang
2011/0042560 A1 2/2011 Ouyang
2011/0101216 A1 5/2011 Musselman
2011/0215798 A1* 9/2011 Beer ............................ 324/214
2012/0006983 A1 1/2012 Cody
2012/0119082 A1 5/2012 Musselman
2012/0145890 A1 6/2012 Goodlett
2012/0199735 A1 8/2012 Krechmer
2012/0208004 A1 8/2012 Wolcott
2012/0223226 A1 9/2012 Rafferty
2012/0280119 A1 11/2012 Musselman
2012/0295276 A1 11/2012 Cooks
2012/0312979 A1 12/2012 Cooks
2012/0312980 A1 12/2012 Whitehouse
2012/0322683 A1* 12/2012 Liu et al. .......................... 506/9
2013/0020482 A1 1/2013 Enke
2013/0037710 A1 2/2013 Wu
2013/0092832 A1 4/2013 Enke et al.
2013/0105683 A1 5/2013 Ouyang
2013/0112017 A1 5/2013 Ouyang
2013/0112866 A1 5/2013 Ouyang
2013/0112867 A1 5/2013 Ouyang
2013/0126723 A1 5/2013 Ouyang
2013/0181010 A1 7/2013 Ouyang
2013/0273552 A1* 10/2013 Ohashi ........................ 435/6.12
2013/0273560 A1 10/2013 Cooks
2013/0330714 A1 12/2013 Cooks
2013/0344610 A1 12/2013 Cooks
2014/0008529 A1 1/2014 Ouyang
2014/0008532 A1 1/2014 Ouyang
2014/0011282 A1 1/2014 Ouyang
2014/0024822 A1* 1/2014 Connolly et al. ........... 536/25.4
2014/0048697 A1 2/2014 Cooks
2014/0051180 A1 2/2014 Cooks
2014/0138538 A1 5/2014 Hieftje
2014/0141466 A1 5/2014 Cooks
2014/0158882 A1 6/2014 Ouyang
2014/0231643 A1 8/2014 Ouyang
2014/0264004 A1 9/2014 Cooks
2014/0299764 A1 10/2014 Ouyang

FOREIGN PATENT DOCUMENTS

GB 2263578 7/1993
JP 50-106694 8/1975
JP 51-120288 10/1976
JP 52-91494 8/1977
JP 60-41748 3/1985
JP 2005-150027 6/2005
WO WO03025973 3/2003
WO WO03081205 10/2003
WO WO2004068131 8/2004
WO WO2005094389 10/2005
WO WO2005104182 11/2005
WO WO2007/103693 9/2007
WO WO2007/140349 12/2007
WO WO2007/140351 12/2007
WO WO2008/046111 4/2008
WO WO2008/054393 5/2008
WO WO2008/082603 7/2008
WO WO2009/023361 2/2009
WO WO2011/072130 6/2011
WO WO2011/106656 9/2011
WO WO2012/100120 7/2012
WO WO2014/120552 7/2014

OTHER PUBLICATIONS

Cody, R.B. et al., "Versatile New Ion Source for the Analysis of Materials in Open Air under Ambient Conditions" Anal. Chem., 2005, 77, 2297-2302.

Cooks, R.G. et al., "Ambient Mass Spectrometry", Science, 2006, 311, 1566-1570.

Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.

Fenn et al., "Electrospray Ionization for Mass Spectrometry of Large Biomolecules," Science, vol. 246, No. 4926, Oct. 6, 1989, pp. 64-71.

Garimella, S. et al., "Gas-flow assisted ion transfer for mass spectrometry", J. Mass Spectrom. 2012, 17, 201-207.

Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.

Haddad, R., et al., "Easy Ambient Sonic-Spray Ionization Mass Spectrometry Combined with Thin-Layer Chromatography," *Analytical Chemistry*, vol. 80, No. 8, Apr. 15, 2008, pp. 2744-2750.

Hill, C.A. et al., "A pulsed corona discharge switchable high resolution ion mobility spectrometer-mass spectrometer", Analyst, 2003, 128, pp. 55-60.

Hiraoka, K. et al., "Atmospheric-Pressure Penning Ionization Mass Spectrometry", Rapid Commun. Mass Spectrom., 18, 2004, pp. 2323-2330.

Hites, Gas Chromatography Mass Spectrometry, Chapter 39, Jun. 24, 1997, pp. 609-626.

Karas, M. et al., "Laser desorption ionization of proteins with molecular masses exceeding 10,000 daltons" Anal. Chem. 1988, 60, 2299-2301.

Kojiro, D.R. et al., "Determination of C.sub.1-C.sub.4 Alkanes by Ion Mobility Spectrometry", Anal. Chem., 63, 1991, pp. 2295-2300.

Leymarie, N. et al., "Negative Ion Generation Using a MAB Source", presented at the Annual Meeting of the American Society of Mass Spectrometry, 2000.

McLuckey, S.A. et al., "Atmospheric Sampling Glow Discharge Ionization Source for the Determination of Trace Organic Compounds in Ambient Air", Anal. Chem., 60, 1988, pp. 2220-2227.

Otsuka, K. et al., "An Interface for Liquid Chromatograph/Liquid Ionization Mass Spectrometer", Analytical Sciences, Oct. 1988, vol. 4, pp. 467-472.

Takáts et al., "Mass Spectrometry Sampling Under Ambient Conditions with Desorption Electrospray Ionization," Science, vol. 306, No. 5695, Oct. 15, 2004, pp. 471-473.

Tanaka, K. et al., "Protein and polymer analyses up to m/z 100,000 by laser ionization time-of-flight", Rapid Commun. Mass Spectrom., 1988, 2, 151-153.

Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.

Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.

International Search Report, Application No. PCT/US2007/63006, Feb. 5, 2008.

Extended European Search Report, Application No. 07757665.0 PCT/US2007/063006 Jan. 7, 2010, 8 pages.

(56) References Cited

OTHER PUBLICATIONS

Article 94(3) European Communication, Application No. 07757665.0 PCT/US2007/063006, Mar. 14, 2012, 9 pages.
International Search Report, Application No. PCT/US2007/69823, Feb. 15, 2008.
Extended European Search Report, Application No. 07797812.0 PCT/US2007/069823, Apr. 4, 2010, 9 pages.
Article 94(3) European Communication, Application No. 07797812.0 PCT/US2007/069823, Jul. 27, 2012, 9 pages.
International Search Report, Application No. PCT/US2007/69821, Feb. 7, 2008.
Extended European Search Report, Application No. 07797811.2 PCT/US2007/069821, Mar. 25, 2010, 9 pages.
European Summons, Application No. 07797811.2 PCT/US2007/069821, Feb. 18, 2013, 39 pages.
International Search Report, Application No. PCT/US2007/81439, Mar. 20, 2008.
Extended European Search Report, Application No. 07844307.4 PCT/US2007/081439, Apr. 14, 2010, 12 pages.
Japanese Office Action, Application No. 2008-558459 PCT/US2007/063006, Jan. 19, 2012, 4 pages.
Unofficial Translation of Japanese Office Action, Application No. 2008-558459 PCT/US2007/063006, Jan. 19, 2012, 5 pages.
Chinese Office Action, Application No. 200780015974.5 PCT/US2007/063006, Feb. 2, 2012, 5 pages.
Chinese Office Action, Application No. 200780015974.5 PCT/US2007/063006, Sep. 25, 2012, 8 pages.
Chinese Office Action, Application No. 200780015974.5 PCT/US2007/063006, Dec. 26, 2012, 7 pages.
International Search Report, Application No. PCT/US2012/000061, Aug. 6, 2013.
Oral Proceedings European Communication, Application No. 07757665.0 PCT/US2007/063006, Mar. 9, 2013, 5 pages.
Korean Patent Application 7024130/2008, Jun. 29, 2013, 6 pages.
Article 94(3) European Communication, Application No. 07797811.2 PCT/US2007/069821, Feb. 2, 2012, 8 pages.
Summons Application No. 07797811.2 PCT/US2007/069821, Feb. 18, 2013, 12 pages.
The AccuTOF-DART Mass Spectrometer, Jan. 1, 2006, pp. 1-6; www.jeolusa.com/SERVICESUPPORT/ApplicationsResources/AnalyticalInstruments/Documents/Downloads/tabid/337/DMXModule/693/CommandCore_Download/Default.aspx?EntryId=171.
Busch, Kenneth L., Desorption Ionization Mass Spectrometry, J. Mass Spectrometry, vol. 30, pp. 233-240 (1995).
Harris, Glenn A. et al., Ambient Sampling/Ionization Mass Spectrometry: Applications and Current Trends, Apr. 15, 2011, Anal. Chem. 2011, 83, pp. 4508-4538.
Harris, Glenn A. et al., Simulations and Experimental Investigation of Atmospheric Transport in an Ambient Metastable-Induced Chemical Ionization Source, Anal. Chem. 2009, 81, pp. 322-329.
Kauppila, Tiina J., et al., Desorption atmospheric pressure photoionization—mass spectrometry in routine analysis of confiscated drugs, Forensic Science International 210 (2011) pp. 206-212.

* cited by examiner

ROBUST, RAPID, SECURE SAMPLE MANIPULATION BEFORE DURING AND AFTER IONIZATION FOR A SPECTROSCOPY SYSTEM

PRIORITY CLAIM

This application is a continuation of (1) U.S. patent application Ser. No. 13/449,615 entitled "ROBUST, RAPID, SECURE SAMPLE MANIPULATION BEFORE DURING AND AFTER IONIZATION FOR A SPECTROSCOPY SYSTEM", inventor: Brian D. Musselman, filed Apr. 18, 2012 which issued Dec. 2, 2014 as U.S. Pat. No. 8,901,488 which claims priority to (2) U.S. Provisional Patent Application Ser. No. 61/476,380 entitled: "ROBUST, RAPID, SECURE SAMPLE MANIPULATION BEFORE DURING AND AFTER IONIZATION FOR A SPECTROSCOPY SYSTEM", inventor: Brian D. Musselman, and filed Apr. 18, 2011, the contents of each of which ((1)-(2)) are herein incorporated by reference in their entireties.

FIELD OF THE INVENTION

The present invention permits desorption ionization of powders, plant materials, and loose substances by securing the position of these materials which are otherwise easily displaced during sample handling and analysis.

BACKGROUND OF THE INVENTION

Ambient pressure desorption ionization sources, such as direct analysis in real time (DART®) and desorption electrospray ionization, enable detection of chemicals present as or embedded in a solid object or condensed on surfaces. Examples of sources include: using a flowing heated gas containing metastable atoms or molecules in DART, using a flowing gas containing ions and metastable atoms or molecules in Flowing Atmospheric Pressure Afterglow (FAPA), and using a flowing high pressure mixture of gas and solvent droplets in desorption electro spray ionization (DESI).

A common occurrence in Homeland Security associated 'security alerts' is the report describing the presence of a "white powder". Identification of such materials requires a determination of composition. Enabling direct determination of composition without the requirement for dissolving the material facilitates reduced sample handling and thus affords greater protection to the humans undertaking the analysis as well as reduced time for analysis.

SUMMARY OF THE INVENTION

In various embodiments of the present invention, metal powders are used to disperse and retain samples for analysis. In an embodiment of the invention, a device for ionizing a sample comprises a sampler device for maintaining or constraining the position of the sample relative to the flowing gases and liquids exiting an ionization source. The device further includes a chamber or open region where the sample can be positioned and an entrance into a spectroscopy system where analysis occurs.

BRIEF DESCRIPTION OF THE DRAWINGS

This invention is described with respect to specific embodiments thereof. Additional features can be appreciated from the Figures in which.

DETAILED DESCRIPTION OF THE INVENTION

Figure 1:
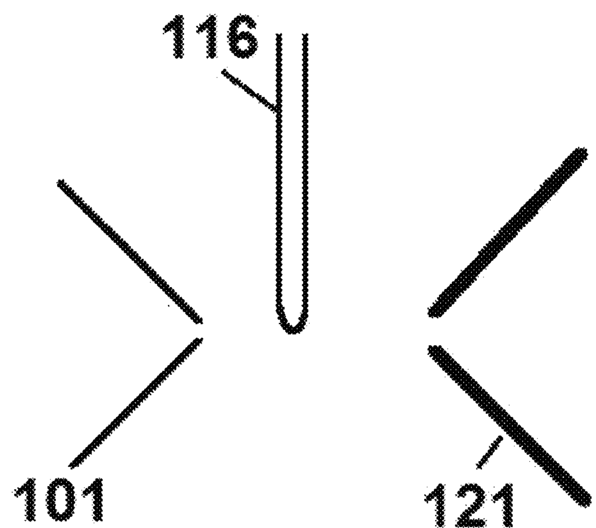
FIG. 1 shows a schematic diagram of a prior art sample device.

The development of efficient desorption ionization sources for use with spectroscopy systems has enabled rapid analysis of samples without requiring laborious sample preparation. These desorption ionization sources require that the sample be positioned in a small region at the exit of the source to permit interaction of the ionizing gases with the sample for analysis.

Atmospheric pressure desorption ionization sources such as direct analysis real time (DART®) and desorption electrospray ionization function well for the ionization of solids and samples adsorbed onto surfaces because they can be fixed in position and not displaced by the action of the flowing gases and solvents. Once formed the ions can, for example, be introduced into a mass spectrometer for mass analysis. However, in the case of chemicals present in powder form, the direct desorption ionization analysis can become problematic due to displacement of the powder by the action of the flowing gases and liquids utilized in the experiment. Without retention of the sample in the desorption ionization region, analysis of these compounds is either compromised and/or results in contamination of the spectroscopy system as the desorbed chemicals contaminate surfaces and entrances to the spectroscopy system.

Thus, for loose powders the utility of the desorption ionization technology is reduced since powders and other light weight or loose samples often cannot be anchored without altering their chemical state (e.g., making into a solution). In an embodiment of the present invention, a simple method to retain powder type samples for surface desorption ionization at atmospheric pressure with increased certainty, involves the co-mixing and thereby the dispersal of a heavy weight powder with the sample powder prior to analysis in order to secure the powder in position. In an embodiment of the present invention, the heavy weight powder can be a metal powder. In an embodiment of the invention, the sample with the metal powder dispersed and therefore coating the sample can be maintained in its position by the weight of the metal powder. In an alternative embodiment of the present invention, the sample with the metal powder dispersed and thereby coating the sample can be maintained in its position by a magnetic field used to fix the metal in position for analysis. In an embodiment of the present invention, a device provides the means for positioning of a sample powder in a desorption ionization region.

In various embodiments of the invention, the metal powder or granules can be selected from the group consisting of metals and non-metals. In various embodiments of the invention, the powder or granules can be selected from the group consisting of magnetic and non-magnetic metals. In various embodiments of the invention, the powder or granules can be one or both a paramagnetic and a ferromagnetic material.

Paramagnetism is a form of magnetism which occurs only in the presence of an externally applied magnetic field. Ferromagnetism is the mechanism by which certain materials form permanent magnets or are attracted to magnets. Classical electro-magnetism indicates that two nearby magnetic dipoles will tend to align in opposite directions, so their magnetic fields will oppose one another and cancel out. However, in ferromagnetic materials the dipoles tend to align in the same direction. The Pauli Exclusion Principle teaches that two electrons with the same spin cannot also have the same 'position'. Under certain conditions, the Pauli Exclusion Principle can be satisfied if the position of the outer orbitals of the aligned electrons is sufficiently distant. In these ferromagnetic materials, the electrons having parallel spins result in the distribution of electric charge in space being further apart and therefore the energy of these systems is at a minimum. The unpaired electrons align in parallel to an external magnetic field in paramagnetic materials. Only atoms with partially filled shells can have a net magnetic moment, so ferromagnetism and paramagnetism only occur in materials with partially filled outer electron shells. Non-magnetic metals typically have filled outer electron shells (e.g., Beryllium, Cadmium, Calcium, Magnesium, Mercury, and Zinc) or form covalently bound molecules fulfilling this condition (e.g., Aluminum, Barium, Copper, Gold, Lead, Lithium, Platinum, Potassium, Radium, Rhodium, Strontium, Silver, Tin, Titanium and Tungsten). As the temperature of ferromagnetic materials increase, the entropy of the system reduces the ferromagnetic alignment of the dipoles. When the temperature rises above the Curie temperature, the system can no longer maintain spontaneous magnetization, although the material still responds paramagnetically to an external field (see Table I for list of ferromagnetic and ferrimagnetic materials and their Curie temperature).

TABLE I

List of ferromagnetic and ferrimagnetic materials and their Curie temperature

| Material | Curie temperature (° K.) |
|---|---|
| Co | 1388 |
| Fe | 1043 |
| $FeOFe_2O_3$ | 858 |
| $NiOFe_2O_3$ | 858 |
| $CuOFe_2O_3$ | 728 |
| $MgOFe_2O_3$ | 713 |
| MnBi | 630 |
| Ni | 627 |
| MnSb | 587 |
| $MnOFe_2O_3$ | 573 |
| $Y_3Fe_5O_{12}$ | 560 |
| $CrO_2$ | 386 |
| MnAs | 318 |
| Gd | 292 |
| Dy | 88 |
| EuO | 69 |

In various embodiments of the invention, the powder or granules can be selected from the group consisting of one or more iron containing substances including Fe, FeO, $FeOFe_2O_3$, $Fe_2O_3$, $MnOFe_2O_3$, $MgOFe_2O_3$, $Y_3Fe_5O_{12}$ and $Fe_3O_4$. In various embodiments of the invention, the powder or granules can be selected from the group consisting of one or more copper containing substances including Cu, CuO, $CuOFe_2O_3$ and $Cu_2O$. In various embodiments of the invention, the powder or granules can be selected from the group consisting of one or more aluminum containing substances including Al and $Al_2O_3$. In various embodiments of the invention, the powder or granules can be selected from the group consisting of one or more nickel containing substances including Ni, NiO, $Ni_2O_3$, $Ni(OH)_2$ and $NiOFe_2O_3$. In various embodiments of the invention, the powder or granules can be selected from the group consisting of one or more cobalt containing substances including Co, $NaCoO_2$ and $Co_3O_4$. In various embodiments of the invention, the powder or granules can be selected from the group consisting of one or more lanthanide metals. In various embodiments of the invention, the powder or granules can be selected from the group consisting of one or more ferromagnetic and/or ferrimagnetic materials of Table I. In various embodiments of the invention, the powder or granules can be selected from the group consisting of physical mixing of two or more of Fe, FeO, $FeOFe_2O_3$, $Fe_2O_3$, $Fe_3O_4$, Cu, CuO, and $Cu_2O$, Al and $Al_2O_3$. In various embodiments of the invention, the powder or granules can be selected from a physical combination of two or more metals or alloys that can either be magnetic or non-magnetic.

When a security alert reports the presence of a "white powder" or other unknown substance, there is an immediate and real need for determining the composition of the powder and specifically whether the powder is anthrax or any other dangerous biological or chemical agent. The first step in analysis of these 'unknowns' often involves isolation of the material in specialized containers for transfer to protect the analyst and his or her environment from contamination. In order to determine the chemical composition or organism present in the powder, the analyst often creates a soluble solution by dissolving the powder in water or an appropriate solvent. The use of expensive and often elaborate testing equipment is needed when using such a soluble solution and since not all powders are soluble valuable time is lost as the analyst labors to create that solution. Ultimately, the sample represents no security threat but the time used in determination of its composition is lengthened by each step of manipulation.

The challenge to rapid chemical analysis is designing a process that uses a minimum of sample manipulation in order to complete chemical analysis in mere seconds. The ability to complete rapid analysis of the sample can be facilitated if real time ionization can be used as a screening method. Thus, the development of a more practical device for positioning samples with minimal human intervention can be an important requirement for deploying real time monitoring, beyond the confines of the laboratory. Utilizing metal powders with ionization techniques to sample and retain the 'unknown' powder and subsequently permit its positioning for analysis can provide a means to facilitate the rapid determination of composition which is necessary to either dismiss or elevate the threat level.

A vacuum of atmospheric pressure is 1 atmosphere=760 torr. Generally, 'approximately' in this pressure range encompasses a range of pressures from below $10^1$ atmosphere=$7.6\times10^3$ torr to $10^{-1}$ atmosphere=$7.6\times10^1$ torr. A vacuum of below $10^{-3}$ torr would constitute a high vacuum. Generally, 'approximately' in this pressure range encompasses a range of pressures from below $5\times10^{-3}$ torr to $5\times10^{-6}$ torr. A vacuum of below $10^{-6}$ torr would constitute a very high vacuum. Generally, 'approximately' in this pressure range encompasses a range of pressures from below $5\times10^{-6}$ torr to $5\times10^{-9}$ torr. In the following, the phrase 'high vacuum' encompasses high vacuum and very high vacuum. The sampler/chamber system can be at atmospheric pressure.

Movement of Samples into and Through the Ionization Region for Analysis

In atmospheric pressure desorption ionization experiments solid objects placed in close proximity to the exit of the source interact with the gas exiting that source. The solid object is often positioned manually or by using devices such as tweezers. In an embodiment of the present invention, a sample in powder form can be immersed into or deposited into a container for co-mixing with metal powder. After mixing to disperse the powder in with the metal, a small fraction of the sample can be removed from the tube along with the metal, enabling its analysis as it is placed in the desorption ionization region. For rapid qualitative determination of samples, the quantity of sample retained on the metal is not critical; therefore, the acquisition of even a small quantity of material can enable a successful analysis. In an alternative embodiment of the present invention, automation of the sampling technology for desorption ionization involves fabrication of a partially glass and partially metal rod sampler tip to which a small magnet can be fixed to cause the magnetized metal coated with "unknown" powder to be retained in its position for analysis. In another embodiment of the invention, by using a microscope slide-sized flat surface (i.e. a flat surface the size of a microscope slide) to which one or more magnets have been fixed on the underside, the metal coated with powder can be deposited on the surface for analysis. In a variety of embodiments of the invention, electro-magnetic fields can be used to automate the movement of the sample from container to container or from container to sample surface for analysis. In an embodiment of the invention, a non-magnetic metal coated with powder can be deposited onto a surface for analysis where the weight of the metal can be sufficient to cause the sample to maintain position in the presence of the flowing gas stream used for desorption ionization.

In an embodiment of the present invention, the mixing of a metal powder with an 'unknown' powder or 'unknown' sample present in crystalline form facilitates mechanical control of the positioning of the sample with magnetic or electro-magnetic fields. A 'sampler device' can be fabricated such that the sample can be inserted into an enclosed chamber attached to a desorption ionization region. Using the 'sampler device' the sample can be reliably transferred from the enclosed chamber into the desorption ionization region by mechanical or electro-mechanical means. In an embodiment of the invention a method is described for depositing the 'unknown' or material of interest onto a sampler and dropping the sampler into the chamber and subsequently manipulating the sampler into position using robotics without requiring human intervention to physically touch or contact the sample. Once the sample is placed in the desorption ionization region, chemical analysis can take place.

A mechanical device is operated by a mechanism. An electro-mechanical device or system is a mechanical device or system that is actuated or controlled by electricity. An electro-magnetic device is operated, actuated or controlled by magnetism produced by electricity. An electro-mechanical force is a force formed by electro-magnetic induction.

Sampler Device

Figure 2:
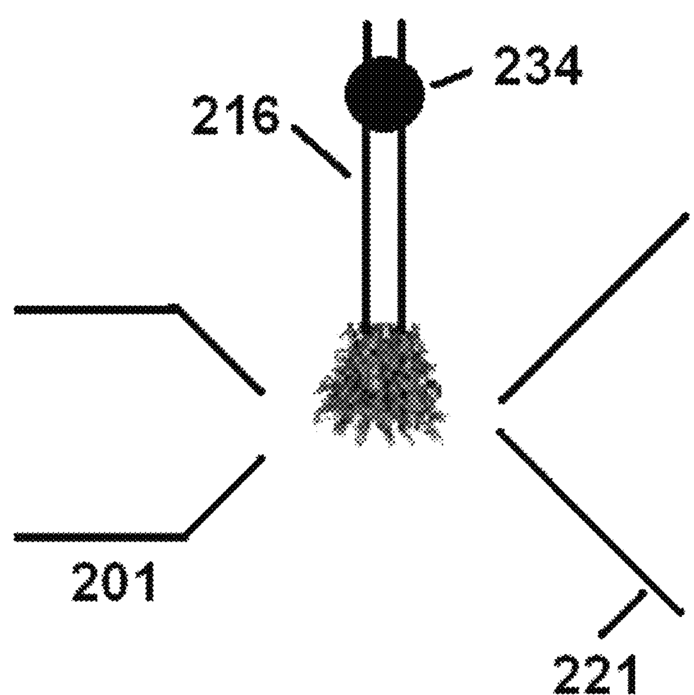
FIG. 2 shows a schematic diagram of a magnetically enabled sampling device according to an embodiment of the invention.
Figure 3:
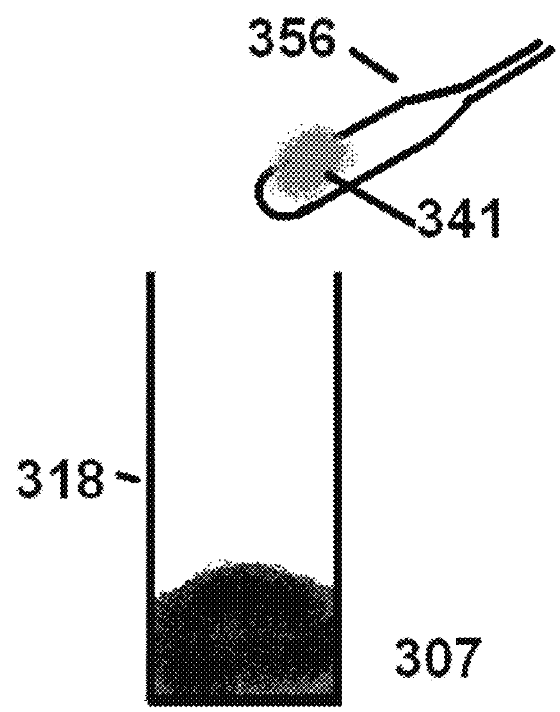
FIG. 3 shows a schematic diagram of the mixing chamber for sample preparation according to an embodiment of the invention.
Figure 4:
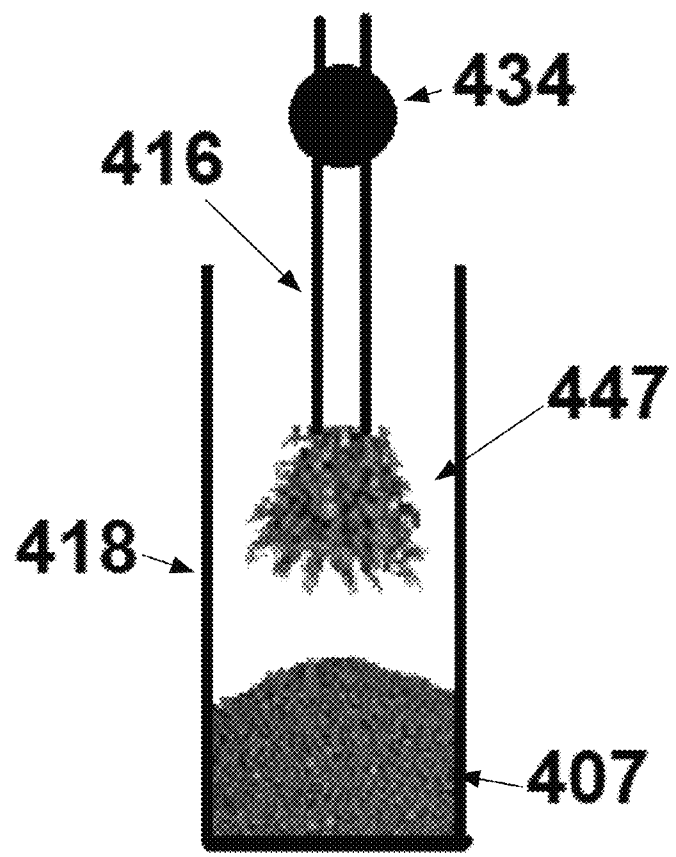
FIG. 4 shows a schematic diagram of sample loading using a magnetically enabled sampling device as shown in the mixing chamber for sample preparation as shown in FIGS. 2 and 3 according to an embodiment of the invention.
Figure 5:
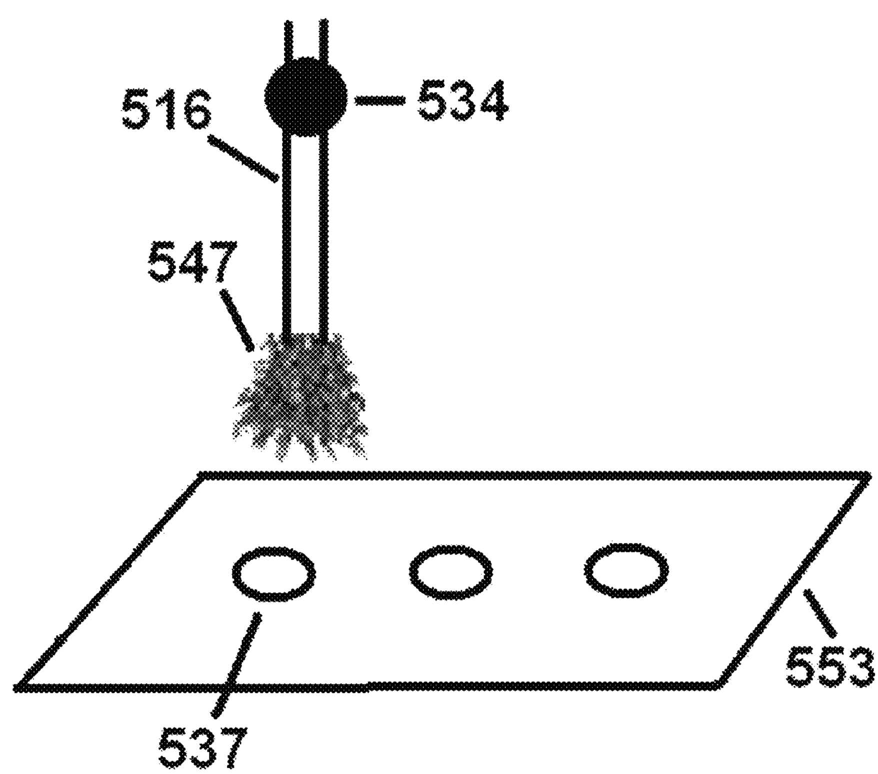
FIG. 5 shows a schematic diagram of the photograph shown in FIG. 6 where sample loading using a magnetically enabled sampling device locates sample on three sites on a surface for analysis according to an embodiment of the invention.
Figure 6:
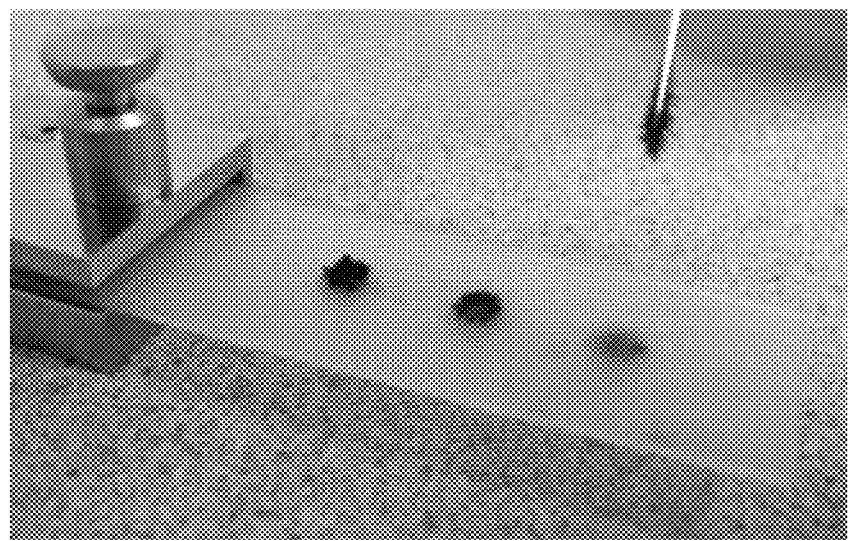
FIG. 6 shows a photograph of sample loading which is using a magnetically enabled sampling device to locate a sample on three sites on a surface for analysis according to an embodiment of the invention.
Figure 7:
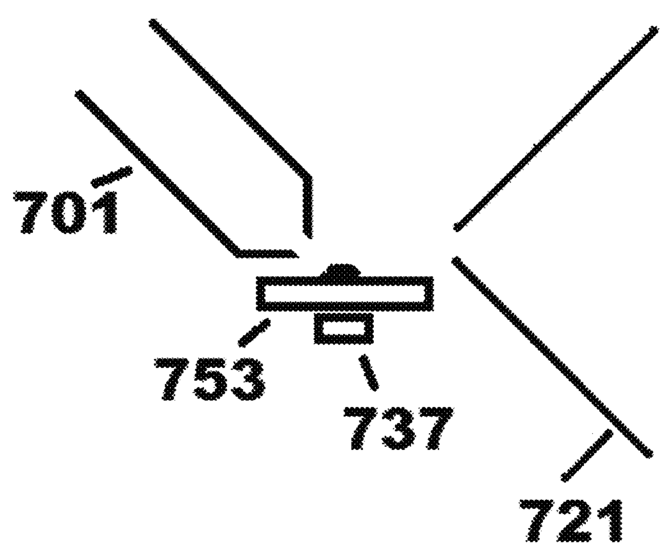
FIG. 7 shows a schematic diagram of an off axis system of analysis enabled with a spectroscopy system as shown in the line drawing of FIG. 10 according to an embodiment of the invention.
Figure 8:
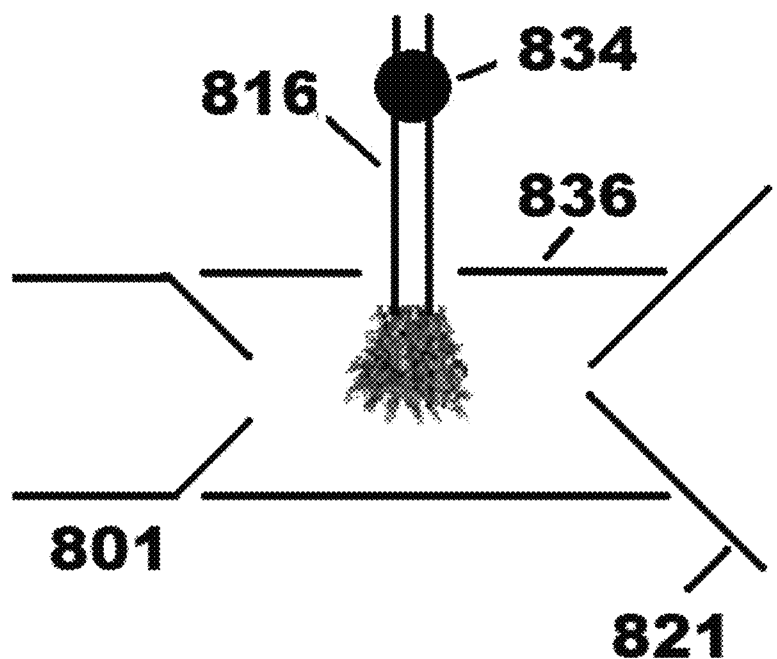
FIG. 8 shows a schematic diagram of the sampling device used to position a sample in a spectroscopy system according to an embodiment of the invention.
Figure 9:
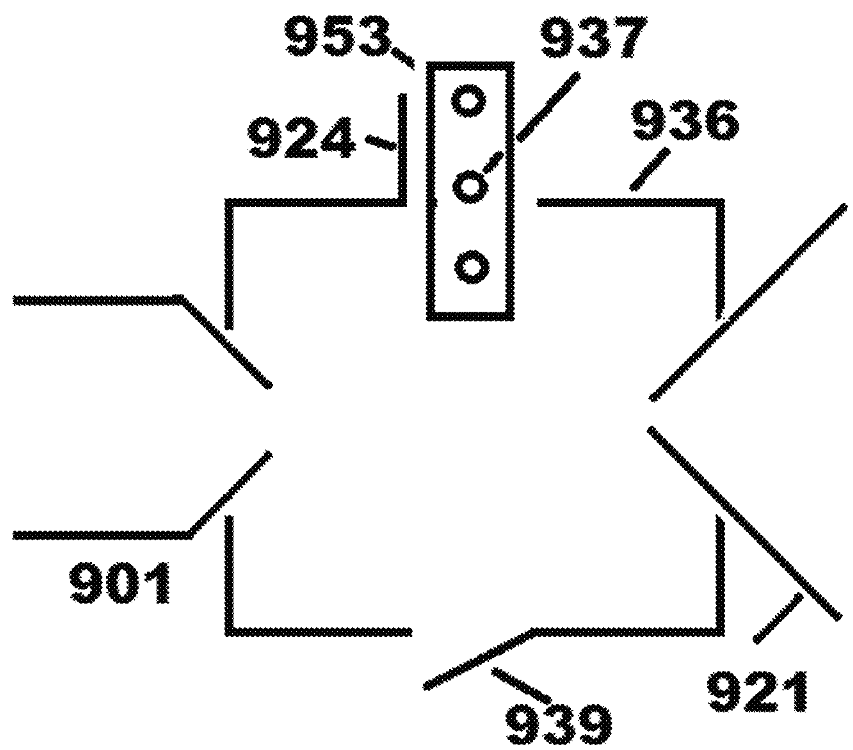
FIG. 9 shows a schematic diagram of the sampling device used to position multiple samples in a spectroscopy system according to an embodiment of the invention.
Figure 10:
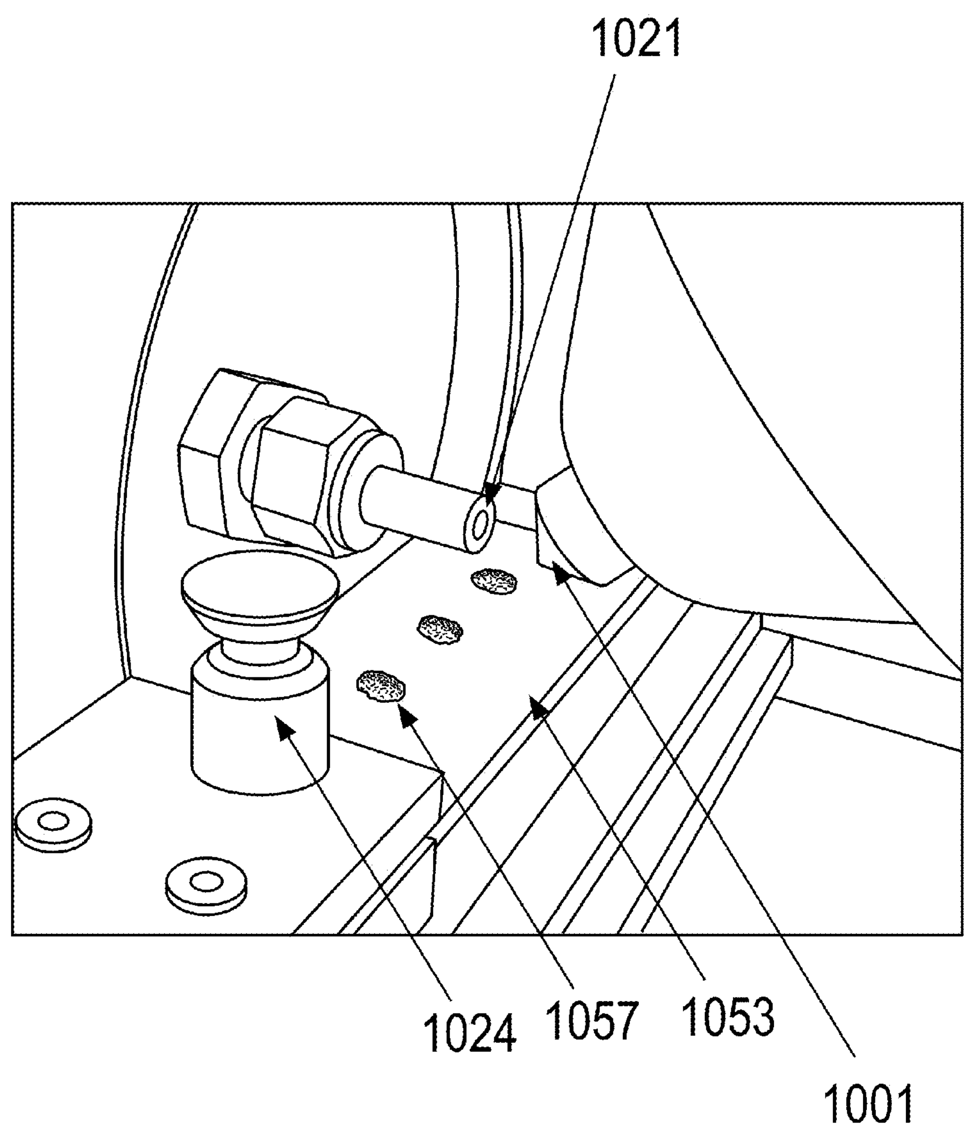
FIG. 10 shows a line drawing of an off axis system of analysis enabled with a spectroscopy system.

FIG. 1 shows prior art of a desorption ionization source coupled to a mass spectrometer. In FIG. 1, the 'sampler device' 116 is a 1.4 mm outside diameter, 0.5 mm inside diameter by 6 mm long glass tube with one end sealed. The sampler device has a coating of material on its exterior surface at the closed end. The coating was generated by dissolving the sample in a solvent and then applying a solution to the sampler device 116. The device 116 is positioned between the ionization source 101 which is directing a flow of gas or liquid at the device 116. Materials desorbed from the surface are ionized and those products enter the spectrometer through an atmospheric pressure inlet 121. In various embodiments of the invention, as shown in FIG. 2, one or more small magnets or pieces of either paramagnetic or ferromagnetic susceptible metal 234 are secured to a metal rod 216 having similar dimensions to the glass rod of FIG. 1. The device 216 can be positioned between the ionization source 201 which is directing a flow of gas or liquid at the device 216. Materials desorbed from the surface can be ionized and those products can enter the spectrometer through an atmospheric pressure inlet 221. A sample of magnetic susceptible metal powder or granules co-mixed with sample powder can then be applied to the closed-end of the tube of the sampler. Preparation of the sample for analysis is depicted in FIG. 3 where a powder sample 341 represented on a common laboratory spatula 356 is added to a container 318 containing an excess of metal 307. As shown in FIG. 4 after mixing of the sample with the metal powder in the container, the metal sampler device 416 to which one or more small magnets or pieces of magnetic susceptible metal 434 have been secured can be inserted into the volume of the container 418 containing an excess of metal powder coated with the sample 407 to permit collection of a portion of the metal powder coated with sample 447. In an embodiment of the invention shown in FIG. 5 the sampler device 516 is a small magnetically susceptible piece of metal such as an iron nail to which a small magnet 534 has been positioned approximately one (1) inch above the closed end of the nail 516, referred to as a 'magnetized nail' 516. The magnetized nail 516 can be used as a sample transfer device to move sample from the container 418 shown in FIG. 4 to a surface for sampling. In FIG. 5 sample positioning of sample (mixed with metal powder 547) for analysis is facilitated by using a surface 553 under which a small magnet 537 or series of magnets can be placed in order to retain the magnetically susceptible metal powder coated with sample in position for analysis. A photograph of the device described in FIG. 5 is shown in FIG. 6. Implementation of the device of FIG. 5 with a direct analysis in real time ionization source is shown schematically in FIG. 7. FIG. 7 shows the surface 753 with magnet 737 positioned to locate sample positioned between the ionization source 701 which is directing a flow of gas or liquid at the sample. Materials desorbed from the surface are ionized and those products enter the spectrometer through an atmospheric pressure inlet 721. A line drawing of the device of FIG. 7 with a direct analysis in real time ionization source is shown in FIG. 10. In an embodiment of the invention shown in FIG. 8, the end of the metal powder coated sample device 816 (utilizing a magnet 834 to hold the sample) can be positioned inside a sampling chamber 836 to allow sampling in a closed volume to protect the analyst from harmful chemicals and toxins. The end of the sampling device 816 can be positioned between the ionization source 801, which can be directing a flow of gas or liquid at the device 816. Materials desorbed from the surface can be ionized and those products enter the spectrometer through an atmospheric pressure inlet 821. In an embodiment of the invention shown in FIG. 9, the sampler device 953 can be inserted through port 924 and positioned inside a sampling chamber 936 to allow sampling in a closed volume to protect the analyst from harmful chemicals and toxins. The sampler device 953 can be positioned between the ionization source 901 which can be directing a flow of gas or liquid at the sampler device 953. Materials desorbed from the surface can be ionized and those products can enter the spectrometer through an atmospheric pressure inlet 921. Orientation of the sampler device 953 can be manipulated without concern for loss of sample since the action of the magnetic field derived from the small magnets 937 retains the sample on the surface. Once analysis is complete the sampler device 953 can exit the chamber 936 through port 939. The sample can be manipulated in the closed environment to permit analysis.

Electro-Mechanical Chamber

In an embodiment of the present invention, the 'electro-mechanical chamber' can be a cylinder having an opening through which the sampler can be inserted. The open 'electro-mechanical chamber' can be of sufficient dimension to permit insertion of a variety of objects. In an embodiment of the present invention, the open 'electro-mechanical chamber' can accept $1\times10^{-4}$ m diameter tubes. In an alternative embodiment of the present invention, the open 'electro-mechanical chamber' can accept $1\times10^{-3}$ m diameter tubes. In another embodiment of the present invention, the open 'electro-mechanical chamber' can accept $1\times10^{-2}$ m diameter tubes. In another alternative embodiment of the present invention, the open 'electro-mechanical chamber' can accept $1\times10^{-1}$ m diameter tubes. In various embodiment of the present invention, the open 'electro-mechanical chamber' can accept a non-cylindrical sampler device.

In an embodiment of the invention shown in FIG. 7 a sampler with the configuration shown in FIG. 5 can be depicted as a plate 753 with the ionization gun 701 directing species at the sample which forms ions that enter the spectrometer through aperture 721. As shown in FIG. 10 the sampler with the configuration shown in FIG. 5 is depicted as a rectangular plate 1053 with the sample mixed with metal powder 1057 has been deposited, with the ionization gun 1001 directing species at the sample which forms ions that enter the spectrometer through aperture 1021. The location of the sample mixed with metal powder 1057 in front of the ionization gun 1001 can be changed using a location locking device 1024. The rectangular plate 1053 enters the proximal end of the 'electro-mechanical chamber. FIG. 9 illustrates a series of events starting with capture of the 'sampler device' 953 in a fixed position such that the sample itself does not touch any surface of the 'electro-mechanical chamber'. The sample may be pushed through an entrance 924 and exit 939 of the chamber to permit rapid, safe detection of powder with the spectroscopy system 921. In an embodiment of the invention, a series of magnets to which a magnetically susceptible metal coated powder of interest can be positioned along a conveyor belt serves to transfer the powder coated metal to the desorption ionization region by using an electro-magnetic field. The interaction of the sample coated magnet with the electro-magnet element serves to hold the sampler in an intermediate position prior to analysis. A sampling zone 901, where the analysis occurs, can be at the distal end of the 'electro-mechanical chamber' of the desorption ionization source. At the proximal end of the 'electro-mechanical chamber a lid capable of closing and forming an airtight seal once the sampler had been placed inside the 'electro-mechanical chamber' in a fixed position. The function of the lid can be to maintain enough pressure to keep gases from escaping through the proximal end of the cylindrical 'electro-mechanical chamber'. Closure of the lid can also initiate the sampling sequence by depressing a switch or completing an electrical or optical contact, and thus connecting an initiation event marker of electrical, digital or mechanical design.

In an embodiment of the invention with the 'electro-mechanical chamber' containing the 'sampler device' closed and sealed, the composition of the chemical environment surrounding the sample can be controlled. In an embodiment of the invention, the sealed 'electro-mechanical chamber' can be used to support one or more functions selected from the group consisting of atmospheric pressure chemical ionization; negative ion chemical ionization; prevention of oxidation or reduction of the sample; or exposure of the sample to one or more other ionization sources. With the sampler under the influence of the electro-magnetic field, the sample can be positioned for desorption ionization. In the case where the sample is a large object with one or more distinct surfaces, the electro-magnetic field can be used to move the entire object in order to affect desorption of different areas of the sample by use of the electro-magnetic fields. In the case where the sample requires different ionization conditions using the same ionization source, the electro-magnetic field can be used to move the entire object in order to affect desorption of the same area of the sample with similar DART guns operated at different conditions by use of the electro-magnetic fields.

In an embodiment of the invention, after the analysis is complete and to facilitate analysis of the next sample, the electro-magnetic field can be used to expel the 'sampler device' out from the ionization region from the 'electro-mechanical chamber'. Once the analysis is complete, the electro-magnetic field can either be turned off and a spring mechanism used to release the sampler device, or the electro-magnetic field can be reversed. In an embodiment of the invention, the opening of an exit port door located at the distal end of the 'electro-mechanical chamber' can deactivate the electro-magnetic field elements and release the sampler device allowing the sample to fall under the effect of gravity through the exit port located at the distal end of the 'electro-mechanical chamber'.

In another embodiment of the invention, a series of electro-magnetic devices including rings, plates, balls, or other shapes designed to capture specific objects can be used to transport the sample into the ideal position for desorption ionization. Once the analysis is complete, the series of electro-magnetic rings can be used to eject the 'sampler device' back into the 'electro-mechanical chamber'. In another embodiment of the invention, concerted action of the electro-magnetic fields results in a high throughput apparatus for rapid sampling by desorption ionization at atmospheric pressure.

The sampler device can have a segment of metal comprised of a band of metal or a strip of metal positioned remote from the desorption ionization region. In this manner, the magnetic fields would not deflect or defocus ions that must be transferred to the spectroscopy system for analysis. In an embodiment of the invention the metal or magnets can be enclosed in the body of the sampler at a position remote from the desorption ionization region. The 'sampling device' objects can be made of glass, ceramic, plastic, wood, fabric or other suitable material shaped into tubes, rod, plates, or other objects customized for sampling. The metal pin, crimping cap, shank, brad, staple, wire or band can be inserted into or bonded to the sampling device in order to secure that sample to the sampling object.

The 'sampler device' and the 'electro-mechanical chamber' system can be automatically operated at increased sample turnaround speed without requiring an analyst or other human intervention. A significant utility of the sampler/chamber system embodied in the invention lies in unattended operation which thereby increases sampling speed.

In an embodiment of the invention a device for ionizing an analyte comprises a chamber with at least three ports, where a first port allows the analyte to enter the chamber and the chamber is adapted to mix the analyte with a material using a magnetic field source where the magnetic field source is adapted to constrain the analyte mixed with the material within the chamber. The device further comprises an atmospheric pressure ionization source adapted to be directed at the analyte mixed with the material to form analyte ions which exit out of a second port. The magnetic field source is further adapted to remove the analyte mixed with the material from the chamber through a third port to dispose of the analyte.

In an embodiment of the invention a method of ionizing a sample comprises mixing the sample with a ferromagnetic material with a lower ionization efficiency relative to the sample and constraining the sample mixed with the material using a magnetic field and generating one or more analyte ions of the sample and then using the magnetic field to dispose of the sample.

In an embodiment of the invention a kit for handling a sample for atmospheric pressure ionization comprises a vial adapted to be opened and resealed containing a material, where opening the vial and locating the sample in the vial and resealing the vial mixes the sample and the material. The kit further comprises a probe including a proximal end, a distal end, a coil situated at the distal end and a switch, where the switch is adapted to apply or discontinue an electro-magnetic field through the coil to position the material mixed with the sample onto the probe, where the probe is adapted to enter the vial and thereby position the material mixed with the sample onto the probe for removal from the vial. The kit further comprises an analysis plate with one or both a fixed magnet and an electro-magnet adapted to move the material mixed with the sample from the probe onto the analysis plate while constraining the material mixed with the sample to one or more regions on the plate for atmospheric pressure ionization.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

What is claimed is:

1. A device for ionizing an analyte comprising:

a chamber with at least one port to allow the analyte to enter the chamber and adapted to mix the analyte with a material;

a lid adapted to close and form a seal with the chamber;

a magnetic field source adapted to constrain the analyte mixed with the material within the sealed chamber; and an ionization source directed at the analyte mixed with the material to form analyte ions.

2. The device of claim 1, where the magnetic field source is generated by one or both a magnet and an electro-magnet.

3. The device of claim 1, further comprising controlling the position of the sample in the chamber with one or both the presence and absence of one or both of an electric field and the magnetic field source.

4. The device of claim 1, where the position of the sample can be adjusted relative to the ionization source prior to an ionization event.

5. The device of claim 1, where the position of the sample can be adjusted relative to the ionization source during an ionization event.

6. The device of claim 1, where the position of the sample can be adjusted relative to the ionization source after an ionization event.

7. The device of claim 1, where the ionization source is an atmospheric pressure ionization source.

8. The device of claim 7, where the atmospheric pressure ionization is selected from the group consisting of a Direct Ionization in Real Time source, a desorption electro spray ionization (DESI) source, an atmospheric laser desorption ionization source, a Corona discharge source, an inductively coupled plasma (ICP) source and a glow discharge source.

9. The device of claim 1, further comprising a spectroscopic analyzer adapted to analyze the sample ions.

10. The device of claim 9, where the spectroscopic analyzer is selected from the group consisting of a mass spectrometer, Raman spectrometer, electro-magnetic absorption spectrometer, electro-magnetic emission spectrometer, surface detection spectrometer, differential scanning mobility spectrometer and ion mobility mass spectrometer.

11. The device of claim 1, where the material includes a metal with one or both a magnetic dipole moment and an inducible magnetic dipole moment.

12. The device of claim 1, where the sample is selected from the group consisting of a powder, lyophilized sample, plant material, fine grains, and a loose substance.

13. The device of claim 1, where the material and the sample are physically mixed.

14. A method of disposing of an analyzed sample comprising the steps of:

receiving a sample mixed with a material that is heavier than the sample;

sealing the sample in an analysis chamber adapted to close and form a seal such that no additional sample mixed with the material enters the analysis chamber;

analyzing the sample in the analysis chamber the analyzing comprising directing an ionization source at the sample mixed with the material to form sample ions;

determining the analysis of the sample in the analysis chamber is complete; and removing the sample mixed with the material using a magnetic field to eject the sample from the analysis chamber.

15. The method of claim 14, where the magnetic field is generated by one or both a magnet and an electro-magnet.

16. The method of claim 14, further comprising providing an electric field to position the sample mixed with the material prior to removing the sample.

17. The method of claim 16, further comprising using the magnetic field and the electric field to remove the sample.

18. A method of disposing of an analyzed sample comprising the steps of:

receiving a sample with a material that is heavier than the sample;

inserting the sample with the material in an analysis chamber;

sealing the sample with the material in the analysis chamber adapted to close and form a seal such that no additional sample mixed with the material can enter the analysis chamber;

analyzing the sample in the sealed analysis chamber the analyzing comprising directing an ionization source at the sample mixed with the material to form sample ions;

determining the analysis of the sample in the sealed analysis chamber is complete; and removing the sample mixed with the material using an electro-mechanical device to eject the sample from the analysis chamber.

19. The method of claim 18, further comprising providing an electric field to position the sample mixed with the material prior to removing the sample.

20. The method of claim 18, where the electro-mechanical device opens an exit port to eject the sample.

* * * * *